(12) United States Patent
Watson

(10) Patent No.: US 8,574,162 B2
(45) Date of Patent: Nov. 5, 2013

(54) SYSTEMS AND METHODS FOR DETECTING PULSES

(75) Inventor: James Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1436 days.

(21) Appl. No.: 12/242,908

(22) Filed: Sep. 30, 2008

(65) Prior Publication Data

US 2009/0326395 A1 Dec. 31, 2009

Related U.S. Application Data

(60) Provisional application No. 61/077,092, filed on Jun. 30, 2008, provisional application No. 61/077,130, filed on Jun. 30, 2008.

(51) Int. Cl.
*A61B 5/02* (2006.01)
(52) U.S. Cl.
USPC .......................................... 600/502; 600/500
(58) Field of Classification Search
None
See application file for complete search history.

(56) References Cited

U.S. PATENT DOCUMENTS

| | | | |
|---|---|---|---|
| 5,226,417 A | 7/1993 | Swedlow et al. | |
| 5,558,096 A | 9/1996 | Palatnik | |
| 6,463,311 B1 | 10/2002 | Diab | |
| 6,519,486 B1 * | 2/2003 | Edgar et al. | 600/336 |
| 6,606,511 B1 | 8/2003 | Ali et al. | |
| 6,816,741 B2 | 11/2004 | Diab | |
| 7,044,918 B2 | 5/2006 | Diab | |
| 7,198,604 B2 | 4/2007 | Kolluri et al. | |
| 7,407,486 B2 | 8/2008 | Huiku et al. | |
| 2005/0070774 A1 * | 3/2005 | Addison et al. | 600/323 |
| 2005/0143665 A1 | 6/2005 | Huiku et al. | |
| 2006/0206021 A1 | 9/2006 | Diab | |
| 2006/0258921 A1 | 11/2006 | Addison et al. | |
| 2007/0213624 A1 | 9/2007 | Reisfeld et al. | |
| 2008/0045810 A1 | 2/2008 | Weber et al. | |
| 2008/0077022 A1 | 3/2008 | Baker | |
| 2008/0082009 A1 | 4/2008 | Baker | |

OTHER PUBLICATIONS

Lohman et al., A Digital Signal Processor for Doppler Radar Sensing of Vital Signs, 2001, Report, 4 pages.*

* cited by examiner

*Primary Examiner* — Benjamin P Blumel
(74) *Attorney, Agent, or Firm* — Shvarts & Leiz LLP

(57) ABSTRACT

According to embodiments, systems and methods are provided for detecting pulses in a PPG signal. Local minima and maxima points may be identified in the PPG signal. Each minimum may be paired with an adjacent maximum forming an upstroke segment. Noise may be removed by comparing adjacent segments and ignoring segments that are too long or too large. Notches in the pulse may be identified and ignored by analyzing adjacent segments. Adjacent upstroke segments may be combined as a single upstroke if the lengths of adjacent upstroke segments are about the same, have similar slopes, and the end point of one segment is close to the start point of an adjacent segment. Segments having small temporal or amplitude difference relative to adjacent segments may be disregarded. The remaining segments may represent the pulse upticks. A sliding time window may be used instead to detect pulses in the PPG signal.

12 Claims, 7 Drawing Sheets

SYSTEMS AND METHODS FOR DETECTING PULSES

CROSS REFERENCE TO RELATED APPLICATIONS

This application claims the benefit of U.S. Provisional Application Nos. 61/077,092, filed Jun. 30, 2008 and 61/077,130, filed Jun. 30, 2008, each of which is hereby incorporated by reference herein in its entirety.

SUMMARY

This disclosure relates to processing a photoplethysmograph (PPG) signal and, more particularly, this disclosure relates to detecting physiological pulses in a PPG signal.

A time domain PPG signal is received. Initial processing may be performed on the PPG signal by, for example, filtering the PPG signal to remove high or low frequency noise components. In one embodiment, turning points (e.g., local minima and local maxima points) are identified in the PPG signal. This may be performed by, for example, computing a second derivative of the received PPG signal. Each minima point may be paired with an adjacent maxima point to form an upstroke segment of a pulse. Alternatively, a local maxima point may be paired with a local minima point to form a downstroke segment of the pulse.

Neighboring upstroke segments may be analyzed to remove noise. For example, seven neighboring upstrokes may be analyzed to derive a threshold value that represents their mean or average amplitude or temporal length values. The threshold value may be compared with a particular upstroke segment in question to determine whether the upstroke segment is either too long in time or too large in amplitude. If the particular upstroke segment is too long in time or too large in amplitude relative to the neighboring upstrokes (e.g., represented by the threshold value) the particular upstroke may be ignored or removed as being noise.

Notches or other PUG phenomena may be detected by comparing the length of an upstroke segment to the length of an adjacent upstroke segment. For example, if a detected upstroke segment is five times longer in time or larger in amplitude than an adjacent upstroke segment, then the detected upstroke may be determined to be a notch (e.g., a dichrotic notch, an ankle notch or a shoulder notch) and may be ignored or removed.

If desired, adjacent upstroke segments may be combined to form a single upstroke segment. For example, the lengths and slopes of adjacent upstroke segments may be determined and compared. If the lengths and slopes of the adjacent upstroke segments are about the same and if the end point of one upstroke segment is close in temporal distance and/or in amplitude to the starting point of the adjacent upstroke segment, then the adjacent upstrokes may be combined to form a single upstroke segment. This may remove notches located, for example, in the middle of pulse upstrokes.

In one embodiment, notches in pulse segments of a PPG signal may be identified (and subsequently removed or ignored) by comparing the difference in amplitude, time, or both for each pair of adjacent upstroke segments. Pairs of upstroke segments that have small temporal differences and/or small amplitude differences may be ignored as being artifacts. The remaining pairs of upstroke segments (i.e., the upstroke segments that have not been removed or ignored) may represent the pulses.

In one embodiment, upstroke segments of a pulse may be detected by using a sliding time window. For example, a sliding time window that is slightly larger (e.g., between 1-2 times (e.g., 1.3-1.5) the duration of pulses) may be applied to the received PPG signal. The overall maximum and minimum points within the sliding time window are determined. The upstroke segment formed by the overall maximum and minimum points may identify the upstroke in the pulse. The size of the sliding time window can be determined using a separate module that provides the heart rate of a patient. Alternatively, the initial size of the initial window can be a predetermined size and dynamically adjusted based on changes in pulse temporal lengths or heartbeats.

The detected pulse features (e.g., upstrokes, amplitudes, start and end points of the upstrokes, frequency, and slopes) may be used for further processing (e.g., in continuous, non-invasive blood pressure (CNIBP) for computing pulse transit time by detecting features from a pulse from one or more PPG signals or mapping the heart rate on a wavelet ratio surface for calculating blood oxygen saturation).

BRIEF DESCRIPTION OF THE DRAWINGS

The above and other features of the present invention, its nature and various advantages will be more apparent upon consideration of the following detailed description, taken in conjunction with the accompanying drawings in which.

DETAILED DESCRIPTION

This disclosure generally relates to pulse detection in, for example, a time-domain PPG signal. It should be understood that the received PPG signal may be digital. For illustrative purposes, this disclosure will be described in the context of time-domain PPG signal generated by a pulse oximeter. It should be understood that the PPG signal may also be generated by any other suitable device(s) capable of generating a PPG or any plethysmograph signal.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electro-gastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, or any combination thereof.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption.

Figure 1:
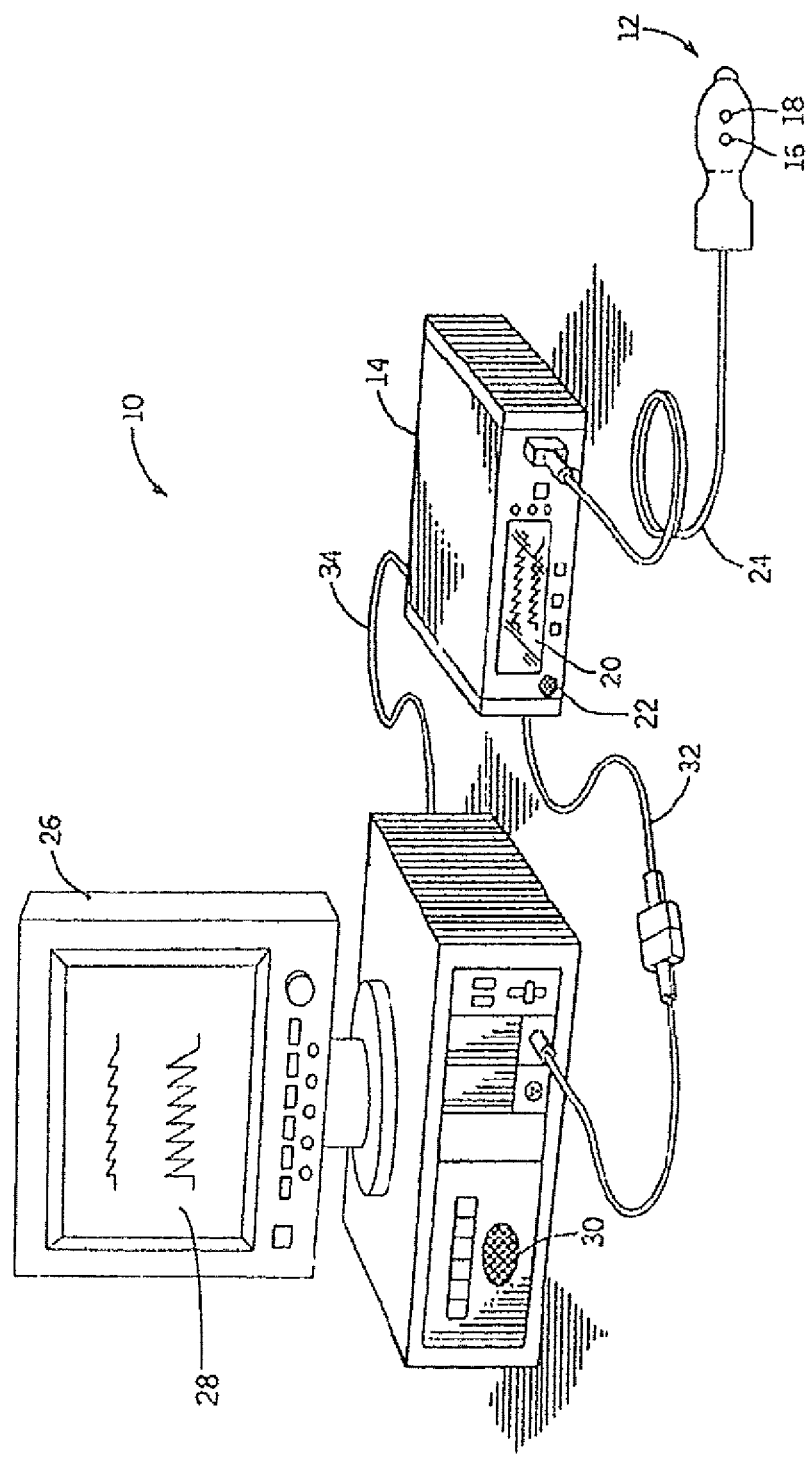
FIG. 1 shows an illustrative pulse oximetry system in accordance with an embodiment.

FIG. 1 shows an embodiment of pulse oximetry monitoring system 10 that may also be used to perform pulse oximetry. System 10 may include a sensor 12 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry or continuous, non-invasive blood pressure (CNIBP) data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., blood pressure) based at least in part on data received from sensor 12 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
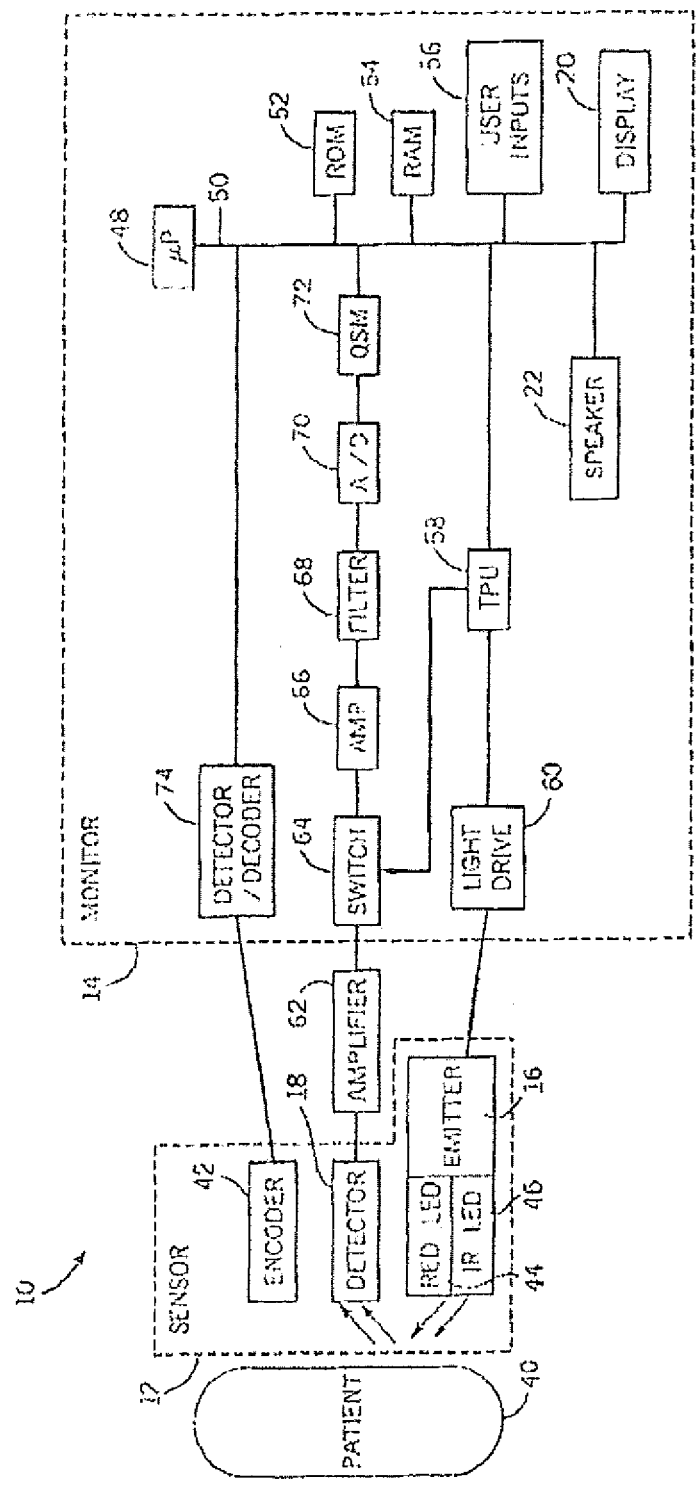
FIG. 2 is a block diagram of the illustrative pulse oximetry system monitoring system of FIG. 1 coupled to a patient in accordance with an embodiment.

FIG. 2 is a block diagram of a pulse oximetry monitoring system, such as system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40. Monitor 14 may also detect the locations of pulses within the signal received from detector 18.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. This information may also be used to select and provide coefficients for equations (associated with the empirical data) from which blood pressure is determined based on an area under a pulse of a PPG signal. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may detect physiological pulses in the PPG signal and determine the patient's physiological parameters, such as blood pressure, $SpO_2$, and pulse rate, using various algorithms and/or look-up tables based on the value of the received signals and/or data corresponding to the light received by detector 18. For example, microprocessor 48 may detect potential pulses in a PPG signal by identifying and pairing each local minimum point with an adjacent local maximum point in the PPG signal to form upstroke segments. In determining whether a detected upstroke is part of a pulse (and not noise), microprocessor 48 may, for example, compare lengths or amplitudes of each adjacent pair of upstroke segments formed by local minimum/maximum points.

Microprocessor 48 may detect notches (e.g., dichrotic notches, ankle notches or shoulder notches) in the UPG signal. If desired, where a notch is detected between two upstrokes, microprocessor 48 may combine the two upstrokes to form a single upstroke (i.e., representing a pulse) when the length, slope and location of the upstrokes suitably match.

Microprocessor 48 may detect and disregard artifacts located off-pulse in the PPG signal and provide pulse information to another component in the system.

In another embodiment, microprocessor 48 may use a sliding time window of a suitable size/length to detect the upstrokes (or downstrokes) in the PPG signal by finding the minimum and maximum points within the sliding time window.

Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Pulse oximetry (i.e., PPG) signals may involve operations that reduce the amount of noise present in the signals or otherwise identify noise components in order to prevent them from affecting measurements of physiological parameters derived from the PPG signals.

Figure 3:
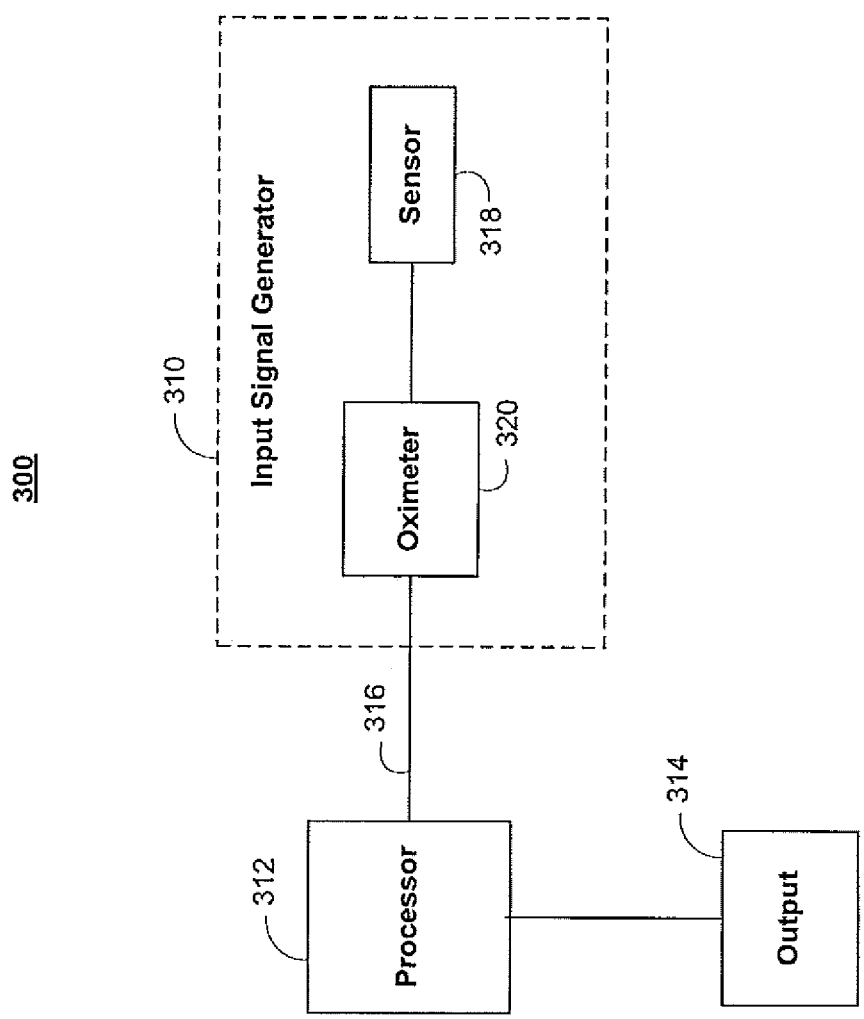
FIG. 3 is a block diagram of an illustrative signal processing system in accordance with an embodiment.

FIG. 3 is an illustrative processing system 300 in accordance with an embodiment. In this embodiment, input signal generator 310 generates an input signal 316. As illustrated, input signal generator 310 may include oximeter 320 (or similar device) coupled to sensor 318, which may provide as input signal 316, a PPG signal. It will be understood that input signal generator 310 may include any suitable signal source, signal generating data, signal generating equipment, or any combination thereof to produce signal 316.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations pulse detection methods of the present disclosure similar to microprocessor 48. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to a calibration device (not shown).

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 212 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10.

Figure 4:
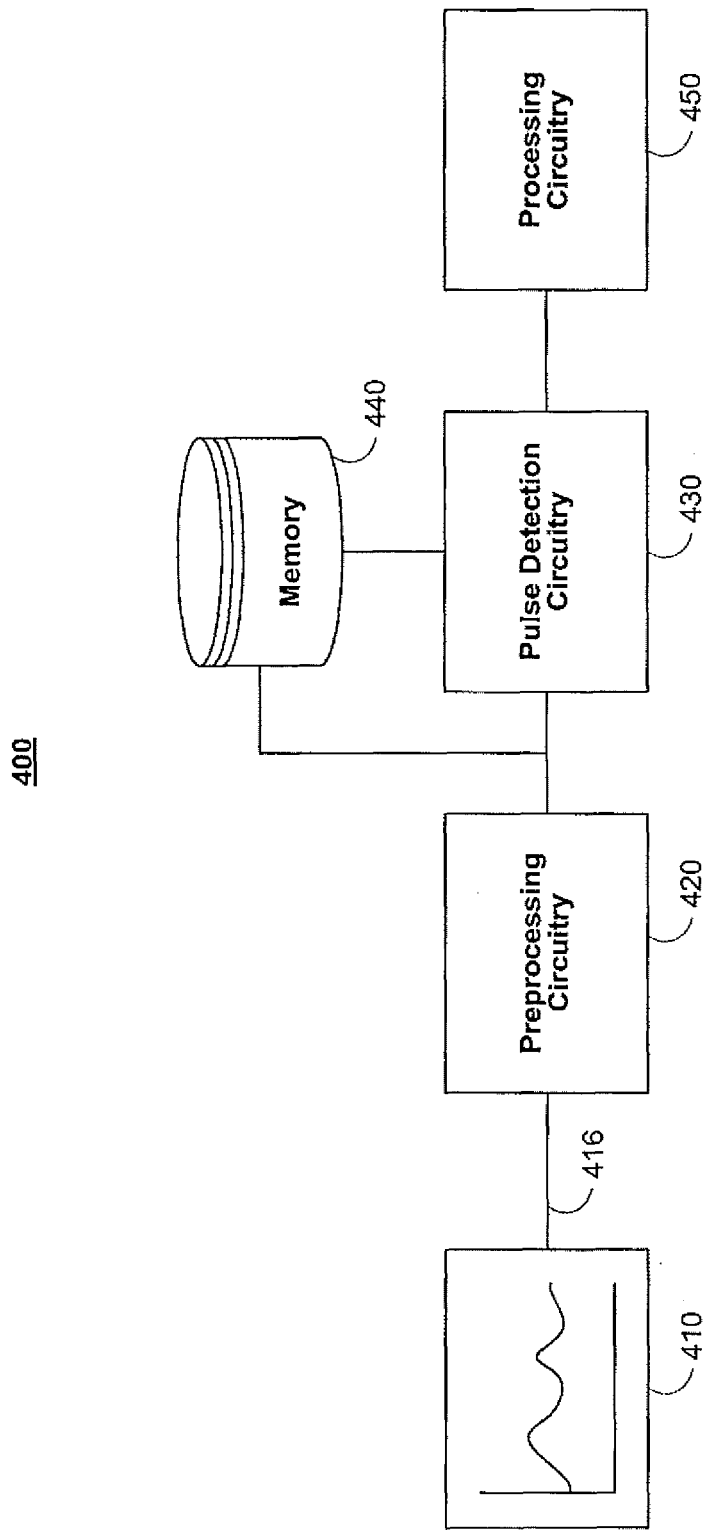
FIG. 4 is block diagram of an illustrative pulse detection system in accordance with an embodiment of the present disclosure.

FIG. 4 is block diagram of an illustrative PPG signal processing system in accordance with an embodiment of the present disclosure. PPG signal processing system 400 may include a PPG signal generation instrument 410 (e.g., sensor 12 (FIG. 2)), preprocessing circuitry 420 (e.g., filter 68), pulse detection circuitry 430, a memory 440 (e.g., ROM 52 or RAM 54) and processing circuitry 450 (microprocessor 48). It should be understood that although each component is drawn separately in FIG. 4, the components may be part of the same device or may be part of different devices in various combinations. For example, PPG signal generation instrument 410 and preprocessing circuitry 420 may be implemented by the same circuitry or device.

Input signal generation instrument 410 generates an input signal 416. Input signal generation instrument 410 may include an oximeter (not shown) coupled to sensor 12 (FIG. 2), which may provide a PPG signal as input signal 416. It will be understood that input signal generation instrument 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, or any combination thereof.

Signal 416 may be coupled to preprocessing circuitry 420. Preprocessing circuitry 420 may be any suitable software, hardware, or both for processing signal 416. For example, preprocessing circuitry 420 may include one or more hardware processors (e.g., integrated circuits), one or more software modules, memory, or any combination thereof. Preprocessing circuitry 420 may, for example, be a computer or may be one or more chips (i.e., integrated circuits). Preprocessing circuitry 420 may perform any suitable signal processing of signal 416 to filter signal 416, such as any suitable band-pass filtering, adaptive filtering, closed-loop filtering, any other suitable filtering, or any combination thereof.

Preprocessing circuitry 420 may be coupled to processing circuitry 450. Processing circuitry 450 may be coupled to any suitable output device such as, for example, one or more medical devices (e.g., a medical monitor that displays various physiological parameters, a medical alarm, or any other suitable medical device that either displays physiological parameters or uses the output of preprocessing circuitry 420 as an input), one or more display devices 20 (FIG. 2) (e.g., monitor, PDA, mobile phone, any other suitable display device, or any combination thereof), one or more audio devices 22, one or more memory devices 52 or 54 (e.g., hard disk drive, flash memory, RAM, optical disk, any other suitable memory device, or any combination thereof), one or more printing devices, any other suitable output device, or any combination thereof.

PPG signal generation instrument 410 may output the generated PPG signal to preprocessing circuitry 420. PPG signal generation instrument 410 may be coupled to preprocessing circuitry 420 or pulse detection circuitry 430 through any wired or wireless communication medium. For example, PPG signal generation instrument 410 may output the PPG signal over BLUETOOTH, 802.11, WiFi, WiMax, cable, satellite, Infrared, or any other suitable transmission scheme.

Figure 5:
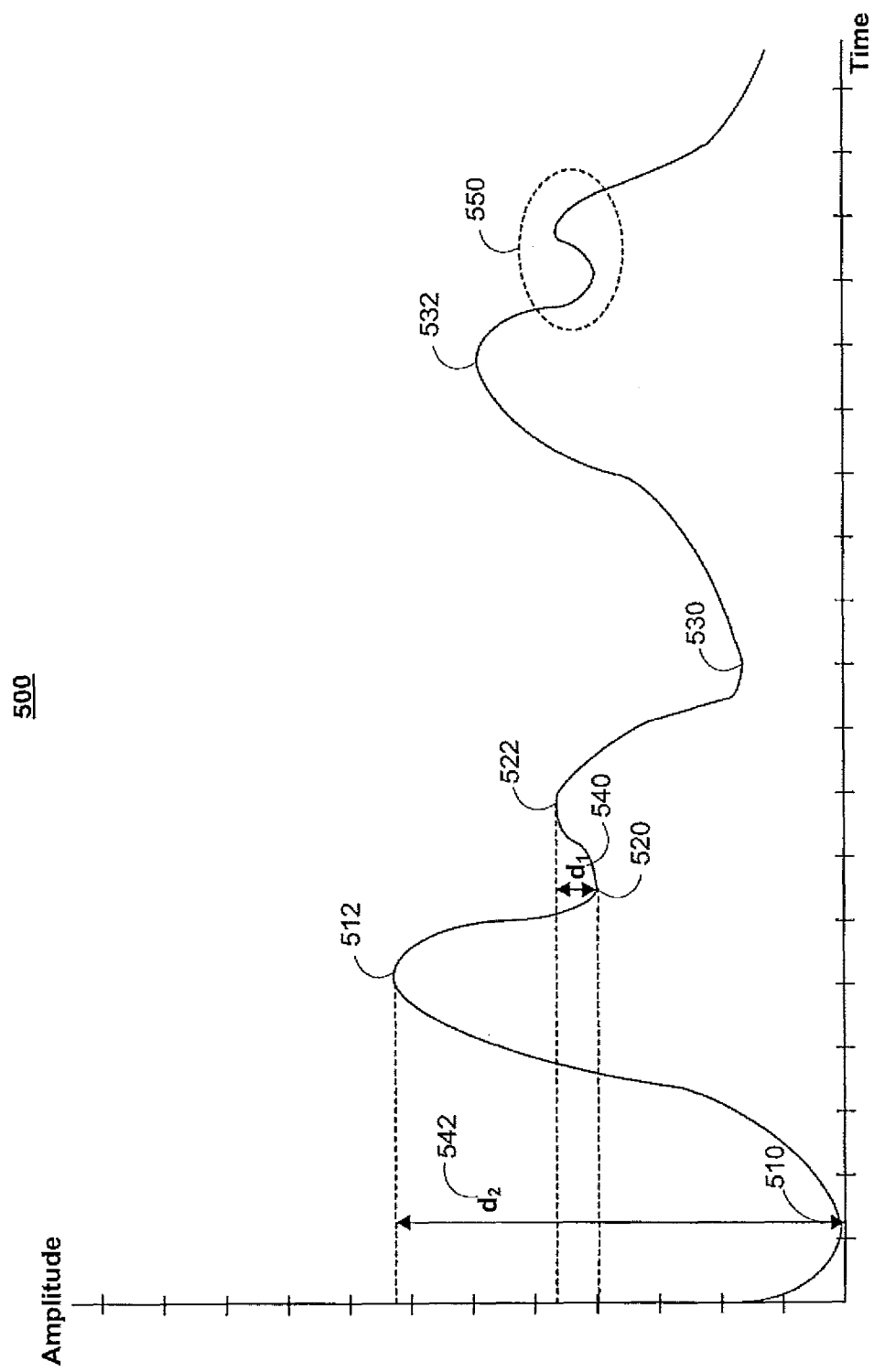
FIGS. 5 and 6 show illustrative PPG signals in accordance with embodiments of the present disclosure.
Figure 6:
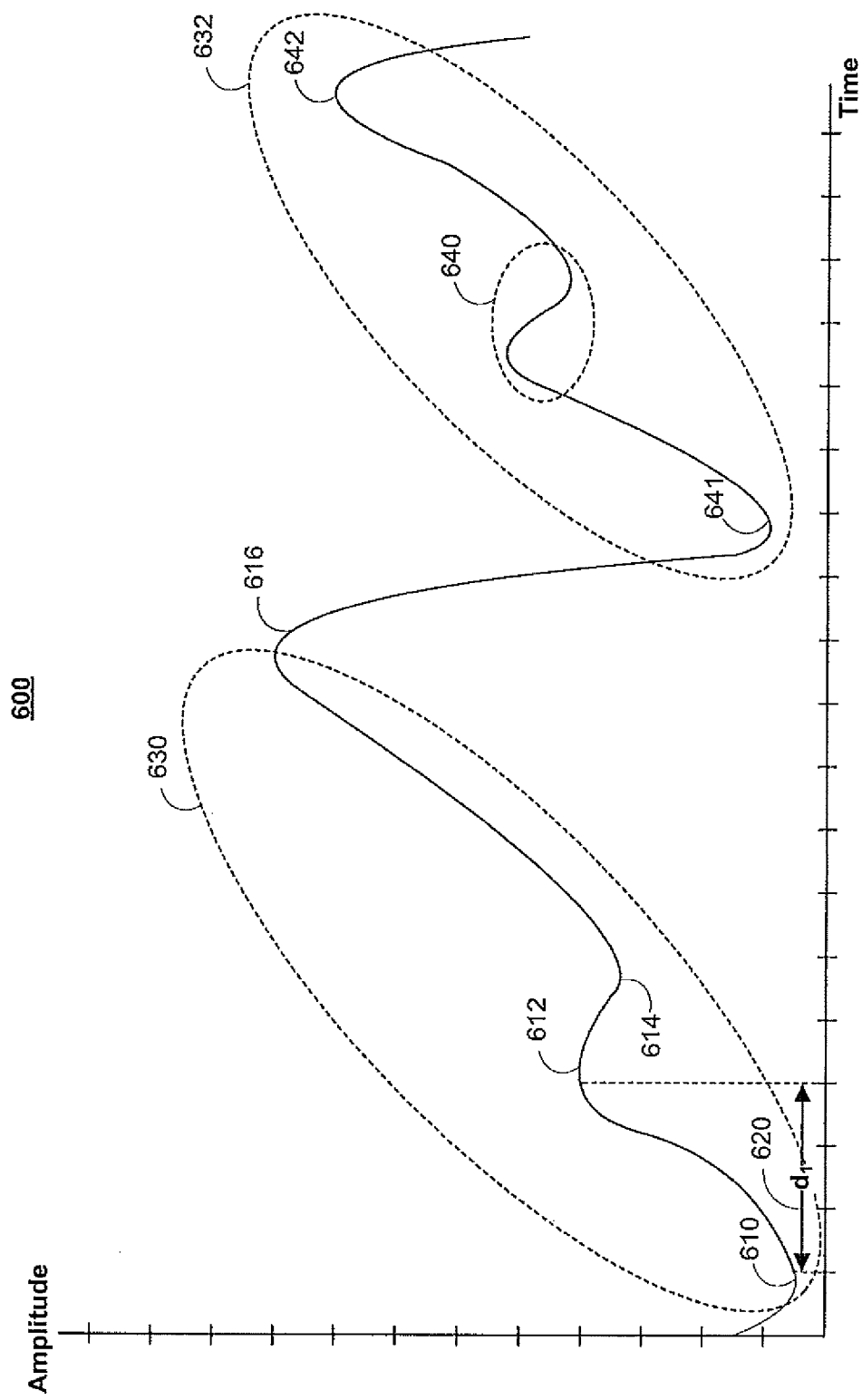

FIGS. 5 and 6 show exemplary PPG signals 500 and 600 that may be output by preprocessing circuitry 420 in accordance with embodiments of the present disclosure.

In an embodiment, preprocessing circuitry 420 may include a Fast Fourier Transform or Inverse Fast Fourier Transform algorithm to convert the received PPG signal into the frequency domain or time-domain respectively. Preprocessing circuitry 420 may also include an analog-to-digital converter or digital-to-analog converter for providing the PPG signal to pulse detection circuitry 430 in a suitable form.

In an embodiment, preprocessing circuitry 420 may be excluded from system 400 and the PPG signal outputted by PPG signal generation instrument 410 may be provided directly to pulse detection circuitry 430. Pulse detection circuitry 430 may perform preprocessing operations on the received signal. Pulse detection circuitry 430 may be implemented by any one or all of the components of monitor 14 (FIG. 2) (e.g., microprocessor 48) or processor 312 (FIG. 3).

Preprocessing circuitry 420 may output the processed PPG signal to memory 440 for storage, to pulse detection circuitry 430, or both. Pulse detection circuitry 430 may process the PPG signal to identify pulses. For example, pulse detection circuitry 430 may detect the upstroke portions, the downstroke portions, or both of the received PPG signal. The resultant series of upstrokes, downstrokes, or both may be processed to exclude those upstrokes, downstrokes, or both attributed to dichrotic notches, other notches (e.g., ankle and shoulder notches), noise, or any combination thereof. As used herein the term ankle notch refers to an artifact that may be present in the PPG signal near the start of the pulse (e.g., near the base of an upstroke) and the term shoulder notch refers to an artifact that may be present in the PPG signal near the top portion of the pulse (e.g., near the peak of the upstroke). The remaining upstrokes, downstrokes, or both may represent detected pulses. In some implementations, ankle notches and shoulder notches may be ignored when representing the pulses. Pulse detection circuitry 430 may operate in real-time on the received PPG signal or may retrieve and store portions of the PPG signal from/to memory 440.

Although the techniques described herein in connection with detecting or identifying pulses are with regard to the detection of an upstroke in a PPG signal (e.g., segments in the PPG signal that have a positive slope between two turning points), it should be understood that similar techniques may be used to detect a downstroke in a PPG signal (e.g., segments in the PPG signal that have a negative slope between two turning points). It is for purposes of clarity and conciseness, and not by way of limitation, that the present disclosure is described with respect to upstrokes.

In one embodiment, pulse detection circuitry 430 may provide pulse information derived from a PPG signal to processing circuitry 450 for use in any suitable application or analysis. In another embodiment, pulse detection circuitry 430 may generate a new signal representing pulses detected from the PPG signal. For example, the new signal may contain a series of upstrokes (or any other suitable indicator) representing a series of pulses. In another embodiment, pulse detection circuitry 430 may generate data about the detected pulses or derived from the detected pulses such as pulse rate, pulse intensity, pulse transit time (e.g., using more than one PPG signal), or any other suitable data. This data may be used to, for example, display, on any suitable display device, the occurrence of a pulse using, for example, ticks, blips, beeps, or any other suitable visual or audible indicator, or any combination thereof. In one suitable arrangement, processing circuitry 450 may be coupled to a display device, which a doctor may view to analyze the patient's condition. Processing circuitry 450 may also perform any or all of these or any other suitable processing operations described with reference to pulse detection circuitry 430.

In another embodiment, pulse features may be used for further processing, for example, in continuous non-invasive blood pressure (CNIBP) measurement or mapping the heart rate on the wavelet ratio surface for calculating $SpO_2$, which is discussed in more detail in U.S. Patent Publication No. 2006/0258921, published on Nov. 16, 2006, which is hereby incorporated by reference herein in its entirety. It will be understood that pulse information derived in accordance with the present disclosure may be used in any suitable application, system, or both.

Figure 7:
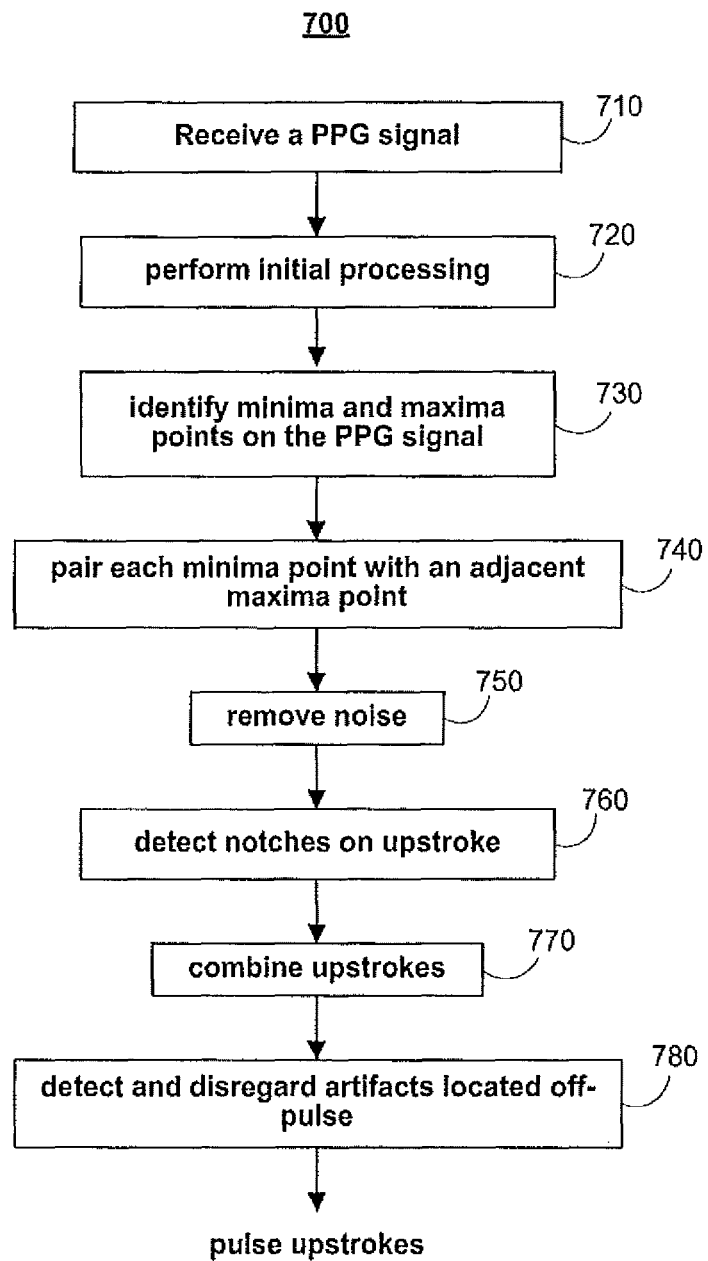
FIG. 7 is a flow chart of illustrative steps that may be performed in an embodiment.

FIG. 7 is a flow chart 700 of illustrative steps performed by pulse detection circuitry 430 (which may also be implemented by microprocessor 48 (FIG. 2)) in accordance with an embodiment of the present disclosure. The processes performed by pulse detection circuitry 430 illustrated in FIG. 7 will be described with continued references to PPG signals 500 or 600 (FIG. 5 or 6).

At step 710, a PPG signal may be received, for example, from preprocessing circuitry 420, instrument 410 (e.g., sensor 12 (FIG. 2) or retrieved from memory 440 (FIG. 4).

At step 720, initial processing may be performed on the received PPG signal. For example, as discussed above, preprocessing circuitry 420 may pass the PPG signal through a band pass filter, low pass filter, high pass filter, comb filter, or any other suitable filter or combination thereof. The filter may remove some high and low frequency noise components in the PPG signal which may simplify and increase the accuracy of pulse detection.

At step 730, local minima and local maxima points are identified in the PPG signal. For example, microprocessor 48 may compute the first or second derivative of the PPG signal (or a portion thereof) to identify turning points in the PPG signal. In one suitable approach, local minimum and local maximum points may be defined as turning points (i.e., points on the PPG signal where the slope changes from positive to negative or negative to positive). For example, as shown in FIG. 5, points 510, 520 and 530 may be identified as local minima points while points 512, 522 and 532 may be identified as local maxima points. Similarly, as shown in FIG. 6, points 610 and 614 may be identified as local minima points while points 612 and 616 may be identified as local maxima points.

At step 740, each minima point may be paired with an adjacent maxima point. For example, to identify upstroke segments, microprocessor 48 may pair each identified minima point (e.g., identified by way of the first derivative) with an identified adjacent maxima point. For example, when searching for upstrokes, a minimum point may be paired with a maxima point located forward in time (i.e., to the right).

Alternatively, when searching for downstrokes, a maxima point may be paired with a minima point located forward in time (i.e., to the right).

In one embodiment, the slope of the segment formed by the two adjacent points may be computed to determine, for example, whether the segment formed by the points is an upstroke or a downstroke. The slope of the segment formed by the two adjacent points may be determined by computing the first derivative of the PPG signal and determining whether the region between the adjacent points is positive or negative. Alternatively, the slope of the segment may be determined to be positive or negative by comparing the two adjacent points to determine which of the two points is larger (i.e., the slope may be determined to be positive when the point later in time is larger than the adjacent point) A positive slope (i.e., when the value of the first derivative of the PPG signal is positive) between the two points may indicate an upstroke in the pulse while a negative slope may indicate a downstroke in the pulse. As defined herein, a pulse includes at least one upstroke segment and at least one adjacent downstroke segment. Within the pulse, there may be further combinations of smaller upstroke and downstroke segments which may indicate dichrotic, shoulder and/or ankle notches (depending on the locations of the segments).

For example, points 510 and 512 of PPG signal 500 may be paired to form a segment. The slope of the segment formed by points 510 and 512 may be determined to be positive which may indicate that the segment is an upstroke portion of the pulse. Also, in PPG signal 600, points 610 and 612 may be paired and points 614 and 616 may be paired (FIG. 6) to form two adjacent upstroke segments of the pulse. As described more fully below, the two segments formed by points 610 and 612 as well as 614 and 616, individually, do not represent upstrokes of pulses. However, they may be combined to form a single upstroke indicative of a single pulse.

At step 750, upstrokes due to noise may be identified and/or removed from the PPG signal. In one suitable approach, microprocessor 48 may identify noise by analyzing a number of neighboring upstrokes (e.g., seven upstrokes) and determining whether a particular upstroke is either too long in time or too large in amplitude relative to its neighbors. Microprocessor 48 may also identify noise by determining whether a particular upstroke is too short in time (e.g., less than 0.1 seconds). The gradient may also be used to determine noise by determining that a particular upstroke has a large peak-to-peak amplitude that occurs over a short period of time. This may be done, for example, by comparing the particular upstroke to a threshold value that may based on a measure of the amplitudes or temporal distances of a number of neighboring upstrokes. In one suitable approach, the threshold value may be based on, for example, a running average or median amplitude value of the previous 3 upstrokes, the current upstroke, and the next 3 upstrokes plus one or more standard deviations or some other suitable amount. Alternatively, the threshold value may be based on an average or median amplitude value of the next 7 upstrokes; the previous 6 upstrokes and the current upstroke; the current upstroke and the next 6 upstrokes; or any other suitable combination of seven or other suitable number of upstrokes.

For example, the upstroke identified by points 510 and 512 may have an amplitude with a value 542 $d_2$. Similarly, the upstroke identified by points 520 and 522 may have an amplitude with a value 540 $d_1$ (FIG. 5). The amplitudes of the remaining upstrokes identified by the remaining points may also be determined. Pulse detection circuitry 430 may store the amplitudes of each of the upstroke segments identified by the paired points in memory 440 (FIG. 4). Pulse detection circuitry 430 may compute a mean, median, average or any other suitable value based on each of the amplitudes and use it to compute the threshold value (e.g., by adding any other suitable value such as, for example, a standard deviation). The threshold value may also be stored in memory 440. Pulse detection circuitry 430 may retrieve the threshold value from memory 440 (FIG. 4) and compare an amplitude of a particular upstroke segment in the PPG signal with the threshold value. Based on the comparison, pulse detection circuitry 430 may determine that the upstroke is noise in the PPG signal (e.g., because the particular upstroke amplitude is larger than the threshold value) and ignore and/or remove the particular upstroke.

In one embodiment, upstrokes due to noise, notches, or other phenomena may be identified by comparing a particular upstroke with a mean or median of the largest 25% (or any other suitable percentage) by amplitude, time, or both of upstrokes (i.e., as opposed to all of the neighboring upstrokes). In another embodiment, upstrokes may be compared against predefined hard limits to remove noise. For example, if an amplitude or temporal distance of an upstroke is determined to exceed a particular hard limit value, the upstroke may be determined to be noise and removed or disregarded. It should be understood that any other parameter (s) of upstrokes may be analyzed to determine presence of noise, notches, or other phenomena.

In one embodiment, pulse detection circuitry 430 may compare the temporal distances of upstroke segments in the PPG signal to remove noise. For example, pulse detection circuitry 430 may measure the distance between a start point and an end point that define a detected upstroke to determine the temporal distance of the upstroke. For example, in PPG signal 600, pulse detection circuitry 430 may measure the distance between points 610 and 612 and assign it a value 620 $d_1$. Pulse detection circuitry 430 may perform a similar measurement for the remaining detected upstrokes and store these values in memory 440. Pulse detection circuitry 430 may compute a mean, median, average value or some other threshold value based on the measured distances and store the threshold value to memory 440 for subsequent retrieval. In one embodiment, the threshold value may be computed based on the measurement of seven or other suitable number of detected upstrokes in a similar manner as discussed above. Pulse detection circuitry 430 may retrieve the threshold value from memory 440 and compare a temporal distance of a particular detected upstroke in the PPG signal with the threshold value. The upstroke segment may be ignored or removed as being noise, a notch, or any other phenomena when the temporal distance of the upstroke segment is larger than the threshold value.

At step 760, notches in pulse upstrokes may be detected. For example, the length of a first upstroke segment corresponding to one pair of local minima and maxima points may be compared with the length of a second adjacent upstroke segment corresponding to another pair of local minima and maxima points. Pulse detection circuitry 430 may determine whether the adjacent upstrokes are substantially longer in time or substantially greater in amplitude (e.g., five times longer or greater) relative to each other. If the length of the second upstroke segment is relatively longer or greater than the length of the first upstroke segment, then pulse detection circuitry 430 may determine the first upstroke to be a notch (e.g., dichrotic, ankle or shoulder notch). Pulse detection circuitry 430 may ignore or remove upstroke segments that are determined to be notches.

In one embodiment, pulse detection circuitry 430 may determine whether the temporal length or amplitude, or both of the first upstroke is relatively greater than one or more threshold values. The threshold value(s) may be computed based on a running average, median, maximum, minimum or some other suitable measure of neighboring upstrokes (e.g., seven neighboring upstrokes). If the temporal length, amplitude, or both of the first upstroke is relatively shorter than the threshold(s), then pulse detection circuitry 430 may determine the first upstroke to be a notch. Alternatively, pulse detection circuitry 430 may compare the first upstroke to the length or amplitude of one or more upstrokes already determined to be pulse portions. If the length or amplitude of the first upstroke is relatively shorter or smaller than that of other pulse segments, pulse detection circuitry 430 may determine the first upstroke to be a notch.

For example, as shown in FIG. 5, the upstroke segment identified by points 520 and 522 may be determined to be a notch because the length of the upstroke segment identified by points 520 and 522 may be relatively smaller than the length of upstroke segment identified by points 510 and 512 (or points 530 and 532). PPG signal 500 is also shown to include the dichrotic notch 550. It should be understood that step 760 may be optional and may be skipped or excluded in some implementations as length may be computed at step 770 (discussed below) in a similar manner as step 760.

In one embodiment, instead of ignoring small upstrokes (e.g., because they are determined to be notches), adjacent upstrokes may be spliced together under certain circumstances. For example, in FIG. 6, dichrotic notch 640 may cause two upstrokes to be detected. Because dichrotic notch 640 is still part of a pulse, the two detected upstrokes may be spliced together to form a single upstroke 632 defined by points 641 and 642. Any suitable criteria may be used in determining whether to splice two neighboring upstrokes.

At step 770, upstrokes may be spliced together. For example, upstrokes corresponding to adjacent pairs of points may be compared. Pulse detection circuitry 430 may determine whether the lengths of the adjacent upstrokes are similar (e.g., within a range of twice the size as the adjacent upstroke) and whether the slopes of the adjacent upstrokes are similar (e.g., within a range of twice the size as the adjacent upstroke). For example, upstrokes that are more than twice as large and less than twice as small as an adjacent upstroke may be ignored. If the adjacent upstrokes have similar length and slope, then they may be combined to form a single upstroke if the end point of a first upstroke (e.g., local maxima point 612 of a first upstroke segment) is relatively close in temporal distance (e.g., within 5-10% of the temporal length of the longer of the two segments) to the starting point of the adjacent upstroke segment (e.g., local minima point 614 of a second adjacent upstroke segment). This may remove notches located, for example, in the middle of pulse upstrokes.

At step 780, artifacts located off-pulse may be detected and removed or disregarded. Artifacts may be noise in the PPG signal that appear between two pulses. Artifacts may be detected by determining the difference in amplitude and/or time for each pair of points. For example, amplitude 540 represents the difference in amplitude between pair of points 520 and 522 (FIG. 5). Similarly, temporal distance 620 represents the temporal difference of points 610 and 612. Pairs of points that have relatively small temporal differences and/or small amplitude differences may be disregarded as being artifacts. For example, if the temporal distance between a pair of points is less than 0.1 seconds or greater than 1 second, the segment identified by the pair of points may be disregarded as being noise.

The remaining pairs (i.e., the pairs of points that have not been ignored, removed or disregarded by pulse detection circuitry 430) through the end of step 780 may be used to identify the pulse upstrokes (i.e., via the troughs and peaks of the PPG signal). These upstrokes can be used in any suitable way as previously discussed.

It will be understood that the above steps of process 700 are illustrative. Any one of the steps may be modified or removed in a suitable way. The steps may also either be skipped or performed in a different order than that described above. Additional steps may be added to any part of process 700.

In an alternative embodiment, or in combination with the above-described embodiments, pulse detection circuitry 430 may detect pulses in the PPG signal by analyzing a section of the PPG signal through a sliding time window. In this approach, the maximum and minimum points found within the sliding time window may correspond to a pulse upstroke.

This approach avoids the need to account for notches, although noise reduction, as described with regard to step 750 of FIG. 7 may still be performed.

Pulse detection circuitry 430 may apply a sliding time window having a temporal length of 1-2 pulses (e.g., 1.3-1.5 times the temporal length of a pulse) in the PPG signal and analyze the PPG signal section inside of the sliding time window. Pulse length may be determined from an outside source providing, for example, a pulse rate. Alternatively, the pulse length used to determine the window size may be determined according to a sample of pulses identified in the PPG signal.

For example, if the sliding time window in FIG. 5 runs from the intersection of the axes until point 530, then the detected upstroke will be formed between overall minimum and maximum points 510 and 512, respectively (e.g., the points in the PPG signal having the smallest and largest amplitudes or magnitudes on the y-axis). Points 520 and 522, associated with a dichrotic notch would be disregarded.

In one embodiment, the length of the sliding time window may, for example, start out as a predetermined value (e.g., length of 1.5 pulses) and dynamically change based on external or internal conditions of, for example, the patient. For example, a separate module may be attached to the patient and used to monitor the heart rate of the patient. The module may output this information to pulse detection circuitry 430 for use in, for example, dynamically adjusting the temporal length of the sliding time window. For example, if the heart rate of a patient increases, the pulses may become shorter in temporal length and accordingly the temporal length of the sliding time window may be decreased.

The foregoing is merely illustrative of the principles of this disclosure and various modifications can be made by those skilled in the art without departing from the scope and spirit of the disclosure.

What is claimed is:

1. A system for detecting pulses in a signal, the system comprising:
processing circuitry capable of:
receiving an input signal;
detecting local minima and local maxima points in the input signal, comparing segments formed by pairs of the local minima and local maxima points to a number of respective neighboring segments, and
determining based at least in part upon the comparison if each segment is a pulse segment.

2. The system of claim 1 wherein the local minima and local maxima points are turning points.

3. The system of claim 1 wherein the comparing comprises comparing the amplitude of a segment to amplitudes of the number of respective neighboring segments.

4. The system of claim 3 wherein the determining comprises determining that the segment is a pulse segment at least in part on whether the amplitude is greater or less than a threshold value computed based at least in part on the amplitudes of the number of respective neighboring segments.

5. The system of claim 1 wherein the comparing comprises comparing the temporal length of a segment to temporal lengths of the number of respective neighboring segments.

6. The system of claim 5 wherein the determining comprises determining that the segment is a pulse segment based at least in part on whether the temporal length is greater or less than a threshold value computed based at least in part on the temporal lengths of the number of respective neighboring segments.

7. The system of claim 1 wherein the comparing comprises comparing the amplitude of a segment to the amplitudes of a percentage of the number of respective neighboring segments having the greatest amplitudes.

8. The system of claim 7 wherein the percentage is generally 25%.

9. The system of claim 1 wherein the processing circuitry is further capable of generating pulse information based at least in part on the determination.

10. The system of claim 9 wherein the pulse information comprises a signal containing pulse segments, and wherein the generating comprises:
   identifying neighboring segments separated by notches; and
   splicing the neighboring segments to form single pulse segments.

11. The system of claim 1 wherein the processing circuitry is further capable of applying a sliding time window to the input signal, and wherein detecting the local minima and local maxima points comprises detecting the minimum and maximum points in the sliding time window.

12. The system of claim 11 wherein a length of the sliding time window is greater than the temporal length of one pulse, less than the temporal length of two pulses, and adjusted dynamically.

* * * * *